United States Patent
Köpfer

(10) Patent No.: US 11,746,761 B2
(45) Date of Patent: Sep. 5, 2023

(54) SHAPE MEMORY ALLOY ACTUATED FLUIDIC SUBASSEMBLY AND EQUIPMENT INCORPORATING IT

(71) Applicant: ACTUATOR SOLUTIONS GMBH, Gunzenhausen (DE)

(72) Inventor: Markus Köpfer, Stoedtlen-Regelsweiler (DE)

(73) Assignee: ACTUATOR SOLUTIONS GMBH, Gunzenhausen (DE)

( * ) Notice: Subject to any disclaimer, the term of this patent is extended or adjusted under 35 U.S.C. 154(b) by 0 days.

(21) Appl. No.: 18/010,595

(22) PCT Filed: Apr. 27, 2022

(86) PCT No.: PCT/EP2022/061170
§ 371 (c)(1),
(2) Date: Dec. 15, 2022

(87) PCT Pub. No.: WO2022/229247
PCT Pub. Date: Nov. 3, 2022

(65) Prior Publication Data
US 2023/0193882 A1    Jun. 22, 2023

(30) Foreign Application Priority Data
Apr. 27, 2021 (IT) .......................... 102021000010589

(51) Int. Cl.
*F03G 7/06* (2006.01)
*F04B 43/02* (2006.01)
*F04B 17/03* (2006.01)
*F04B 43/09* (2006.01)

(52) U.S. Cl.
CPC .......... *F03G 7/06143* (2021.08); *F04B 17/03* (2013.01); *F04B 43/02* (2013.01); *F04B 43/09* (2013.01)

(58) Field of Classification Search
CPC ...... F04B 43/0072; F04B 43/00; F04B 17/03; F04B 43/02; F04B 2203/04; F03G 7/06143
USPC ...................................... 417/410.1, 415, 416
See application file for complete search history.

(56) References Cited

U.S. PATENT DOCUMENTS

| | | |
|---|---|---|
| 5,325,880 A | 7/1994 | Johnson et al. |
| 7,828,792 B2 | 11/2010 | Mcnally et al. |
| 2010/0008794 A1* | 1/2010 | Rush ..................... F04B 43/043 417/416 |
| 2010/0221124 A1* | 9/2010 | Ikushima ............ F04B 43/0045 417/413.1 |
| 2012/0209189 A1 | 8/2012 | Gray et al. |

OTHER PUBLICATIONS

International Search Report and Written Opinion dated Aug. 19, 2022 in PCT/EP2022/061170, 14 pages.

* cited by examiner

*Primary Examiner* — Philip E Stimpert
(74) *Attorney, Agent, or Firm* — Element IP, PLC

(57) ABSTRACT

The present invention is inherent to a shape memory alloy actuated fluidic subassembly (10) and to an equipment incorporating it as dispensing device, wherein actuation of the shape memory alloy wires (16, 16') causes a fluid-tight reservoir (17") to e compressed by a lid (18) so as to reduce its volume from a maximum volume Vo to a minimum volume V1, this reduction resulting in a pressure increase that causes the opening of an outlet flap (13") and the dispensing of a fluid through an outlet channel (13).

15 Claims, 5 Drawing Sheets

SHAPE MEMORY ALLOY ACTUATED FLUIDIC SUBASSEMBLY AND EQUIPMENT INCORPORATING IT

The present invention is inherent to a shape memory alloy (SMA) actuated fluidic subassembly.

Generally speaking, the use of SMA wires as actuating elements provides various advantages with respect to other actuating systems in terms of weight, power consumption, costs and they exploit the capability of properly trained SMA wires to shorten when heated, most typically by Joule effect through a suitable current supply. A field in which the advantages given by the use of shape memory alloy wires is recognized since a long time is the fluidic valve control, as described in U.S. Pat. Nos. 3,835,659 and 4,973,024, and a particular application where these advantages are of particular relevance is microfluidic valves and the so-called "lab-on-a-chip" application such as described in the paper "Electronic control of elastomeric microfluidic circuits with shape memory actuators" by Vyawahare et al, published in 2008 on labchip, number 8, pages 1530-1535. In this paper, the SMA wire is looped around a flexible channel for controlling its diameter up to its closing. The solution described in this paper is far from ideal for the stress applied to the channel when it needs to be fully closed.

Use of SMA wires in fluidic modules is also described in EP1552146 in which a plunger is driven to reduce to zero a fluid dispensing volume, such solution being not optimal since repeated contact and impact of the plunger may lead to particle release contaminating the dispensed fluid. In the same field, a similar solution is disclosed in US2012/209189 that does not describe how to effectively realize a SMA-based system capable of reliable operations, i.e. subjected to a proper load, and also relies on spring-loaded poppets to close an inlet and an outlet valve through a flexible membrane in contact with the dispensed fluid. More specifically, a not properly designed SMA-based actuator will lead to an excessive fatigue of the SMA wire and its breakage/failure, as outlined in the paper "Thermomechanical fatigue of shape memory alloys" by Lagoudas et al, published in 2009 in Smart Materials and Structures, Volume 18, Number 8.

Purpose of the present invention is to overcome the drawbacks of SMA-based fluidic actuators according to the prior art, and in a first aspect thereof consists in a shape memory alloy actuated fluidic subassembly as detailed in the claims of the present application.

The invention will be further illustrated with the help of the following figures where:

FIGS. 2A-2D are schematic representations of a second embodiment of a shape memory alloy actuated fluidic subassembly according to the present invention, with FIG. 2A being a view from above while FIGS. 2B, 2C, 2D are cross-sectional views taken along line A-A' of FIG. 2A in its rest position (2B), first (2C) and second (2D) actuation statuses;

In the figures, the size and the dimensional ratios of the various elements shown in some cases have been altered in order to help understanding the drawings, with particular but not exclusive reference to the diameter of the SMA wires, the size of biasing elements, such as return springs, and to the length/thickness/width of fluid-tight sealing elements. Moreover, crimping means for the shape memory alloy wires as well as current conductive elements for their activation are not shown, since they are widely known to a person skilled in the art and not necessary for the understanding of the invention.

Figure 1A:
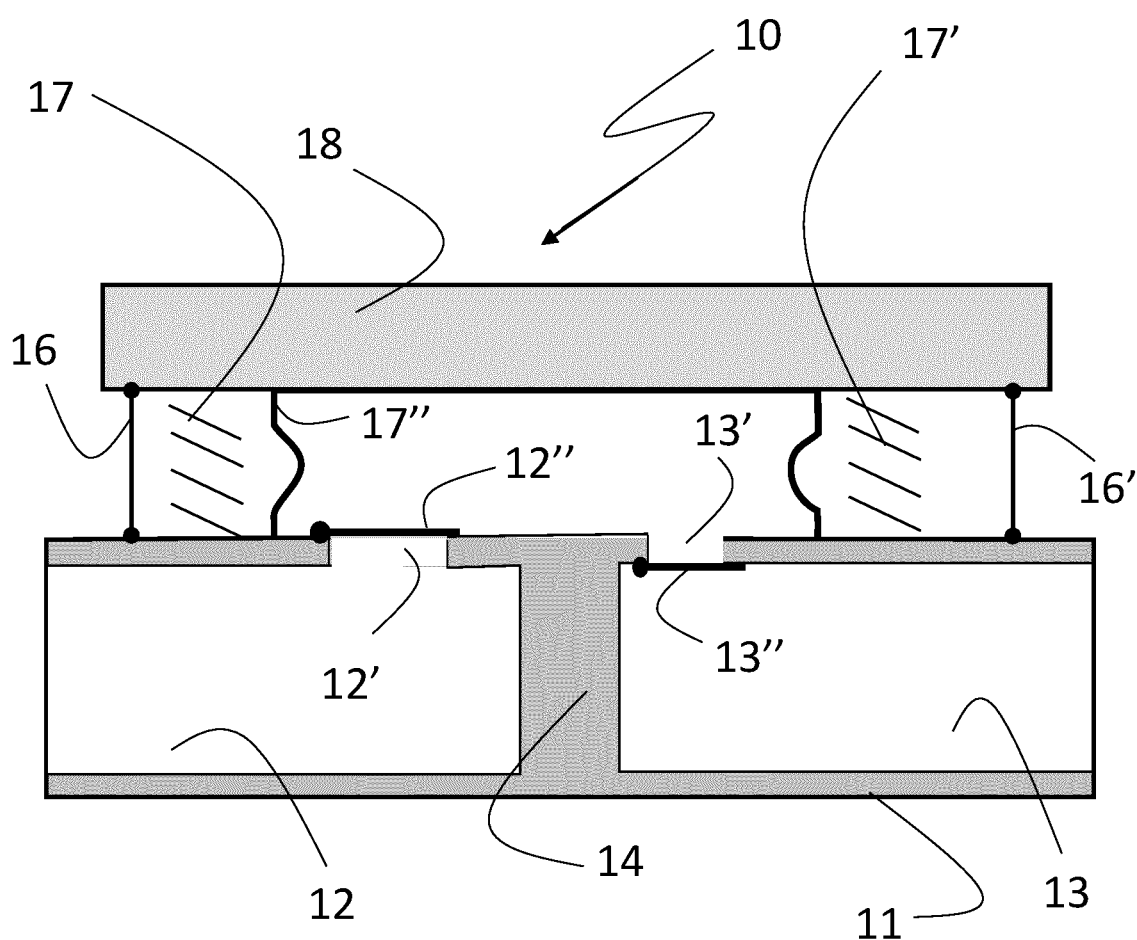
FIGS. 1A-1C are schematic representations of a cross-sectional view of a shape memory alloy actuated fluidic subassembly according to the present invention in its rest position (1A), first (1B) and second (1C) actuation statuses.

A schematic representation of a cross sectional view of a first embodiment of a shape memory alloy actuated fluidic subassembly according to present invention is shown in FIG. 1A. Subassembly 10 has a base 11 with an inlet channel 12 and an outlet channel 13 separated by a wall 14. Inlet channel 12 and outlet channel 13 communicate respectively through inlet port 12' and outlet port 13' with a fluid-tight reservoir defined by a shell 17", preferably made with a rubber material, that is compressible by lid 18 from a maximum volume Vo to a minimum volume V1.

The movement of lid 18 is driven in compression from Vo toward V1 by a couple of shape memory alloy wires 16, 16' connecting base 11 with lid 18, while it is driven in expansion from V1 toward Vo by return springs 17, 17'.

Inlet port 12' and outlet port 13' are normally closed respectively by flaps 12" and 13", meaning that a certain force is required for their opening. The closing force can be provided by various means, for example in the embodiment shown in FIG. 1A, in which flaps 12" and 13" are pivoted on base 11 in abutment thereon, such force could be provided by a torsional loading spring acting also as anchoring element of flaps 12", 13" on base 11. In other words, it is preferred to have ports 12', 13' respectively closed by flaps 12", 13" longer than the port width, which is defined as the width of the opening between the inlet/outlet channels 12, 13 and the fluid-tight compressible reservoir 17.

Figure 1B:
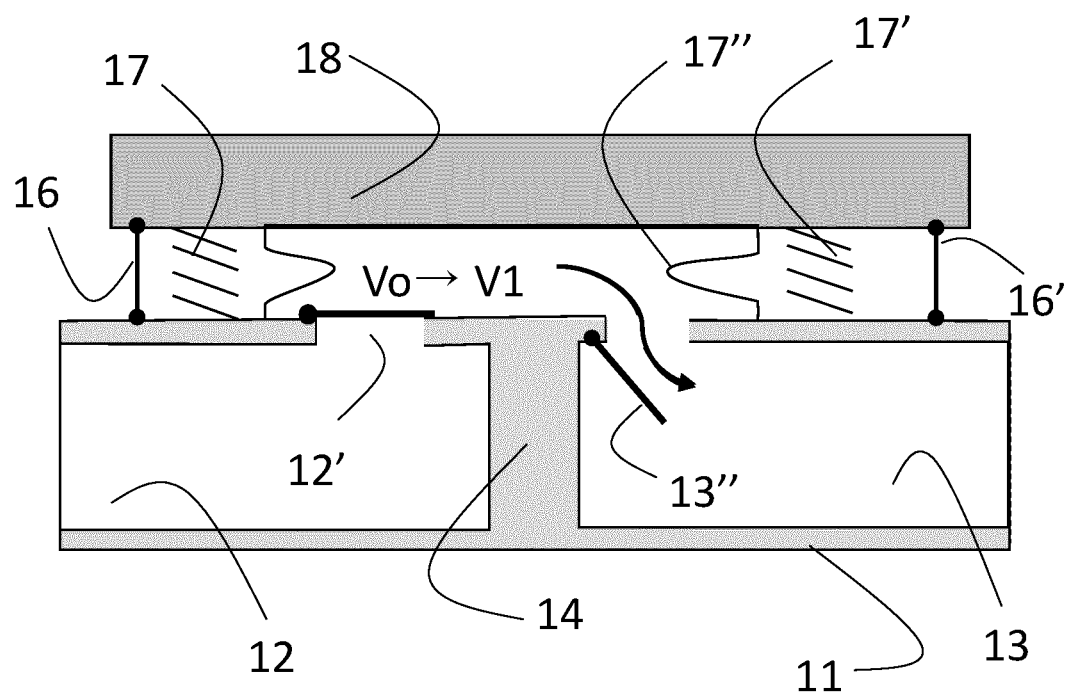
Figure 1C:
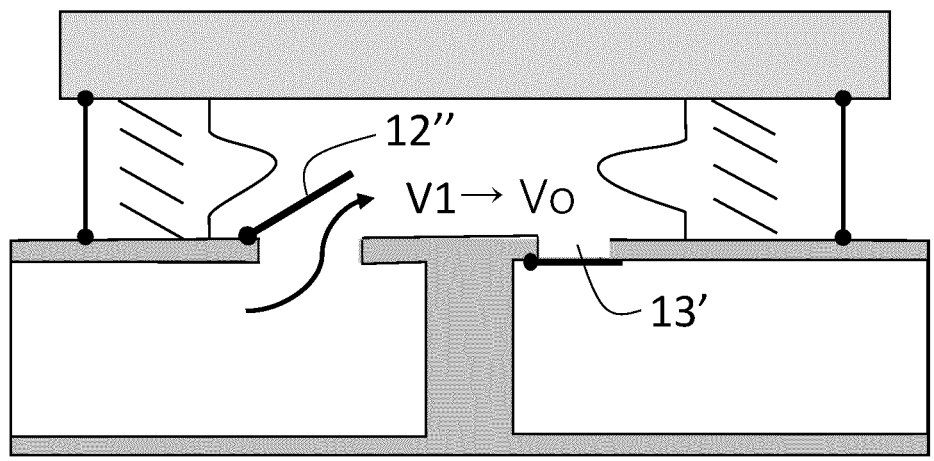
Figure 2A:
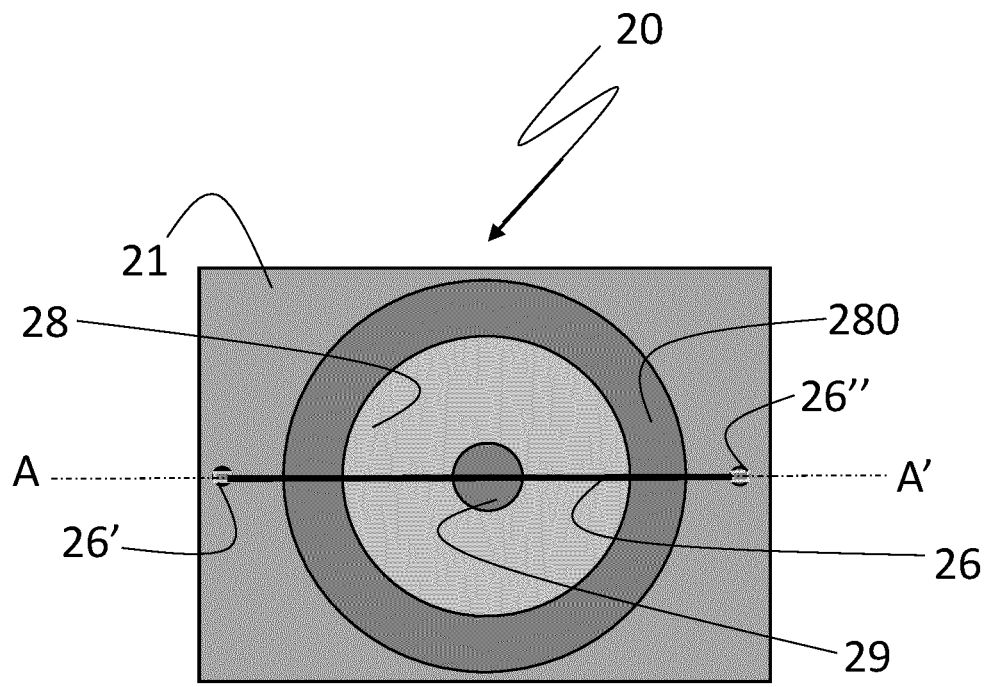

While FIG. 1A is the cross-sectional schematic representation of subassembly 10 from a structural standpoint, FIGS. 1B and 1C are cross-sectional schematic representations of a first actuation state of subassembly 10 such as fluid dispensing (FIG. 1B), and a second actuation state such as fluid loading (FIG. 1C).

In particular, in the dispensing phase, the activation of the shape memory alloy wires 16, 16' and their consequent shortening brings down lid 18 toward base 11 compressing shell 17" and springs 17, 17', thus reducing volume Vo toward V1. The pressure increase is such to overcome the resistance of the torsional spring of flap 13", that is pivoted below outlet port 13', thus rotating flap 13" downwards and allowing to dispense through port 13' a precise amount of fluid (essentially Vo-V1) in a very reproducible way. On the contrary, since flap 12" is pivoted above port 12', the pressure increase in shell 17" will keep port 12' tightly closed thus preventing backflow of the fluid into the inlet channel 12.

After the dispensing phase, the SMA wires 16, 16' are deactivated whereby the return springs 17, 17' move back lid 18 toward its starting position to restore volume Vo. This movement causes a pressure decrease in reservoir 17", leading to the opening of the inlet port 12' through the upwards rotation of flap 12" against the resistance of its torsional spring, and the filling of reservoir 17" through fluid aspiration. On the contrary, since flap 13" is pivoted below port 13', the pressure decrease in shell 17" will keep port 13' tightly closed thus preventing backflow of the fluid from the outlet channel 13.

Needless to say, for the system to go through cyclic dispensing and filling, there is the need of a first cycle with just air going out from outlet port 13', whereas the pressure drop consequent to the SMA wires deactivation and the action of the return springs 17, 17' will fill reservoir 17" with the fluid to be dispensed.

Figure 3:
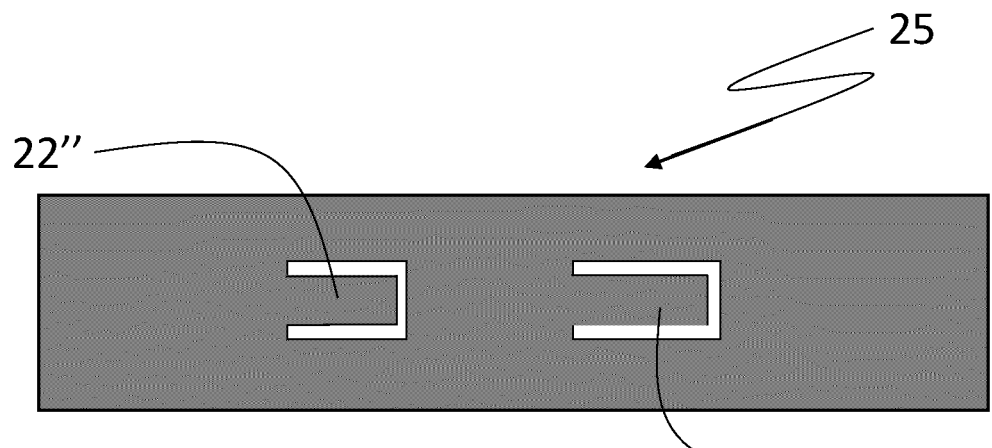
FIG. 3 is a schematic view from above of a preferred way to make the inlet and outlet flaps used in said second embodiment.

Referring now to the second embodiment shown in FIGS. 2A-2D, subassembly 20 has a base 21 with an inlet channel 22 and an outlet channel 23 separated by a wall 24 and put in communication with a fluid-tight reservoir respectively through an inlet port 22' and an outlet port 23' that are normally closed by respective flaps 22" and 23", similarly to the first embodiment described above. The closing force can be provided by various means, for example in the embodiment of FIGS. 2A-3 a preferred way to make flaps 22", 23" is shown in FIG. 3 to be a continuous elastic membrane 25 with two cut-outs shaped as inverted Cs, said membrane 25 being located on the ceiling of channels 22, 23 and passing through wall 24, such that the closing force is provided by the resistance to deformation of the material of membrane 25.

As in the first embodiment, the inlet/outlet ports are closed by flaps that are longer than the port width and abut on the base, but in this case both flaps are located below the respective ports whereby wall 24 extends toward the inlet channel 22 below port 22' in order to provide an abutment for flap 22".

In this second embodiment the fluid-tight reservoir is defined by a dome-shaped elastically deformable element 28, whose periphery is blocked by a gasket 281 held in an annular seat 280 fixed to base 21. A shape memory alloy wire 26 passes over the apex of dome 28 and through suitable grooves that are provided in seat 280, in order to connect to fixing pillars 26', 26" also fixed to base 21.

Figure 2B:
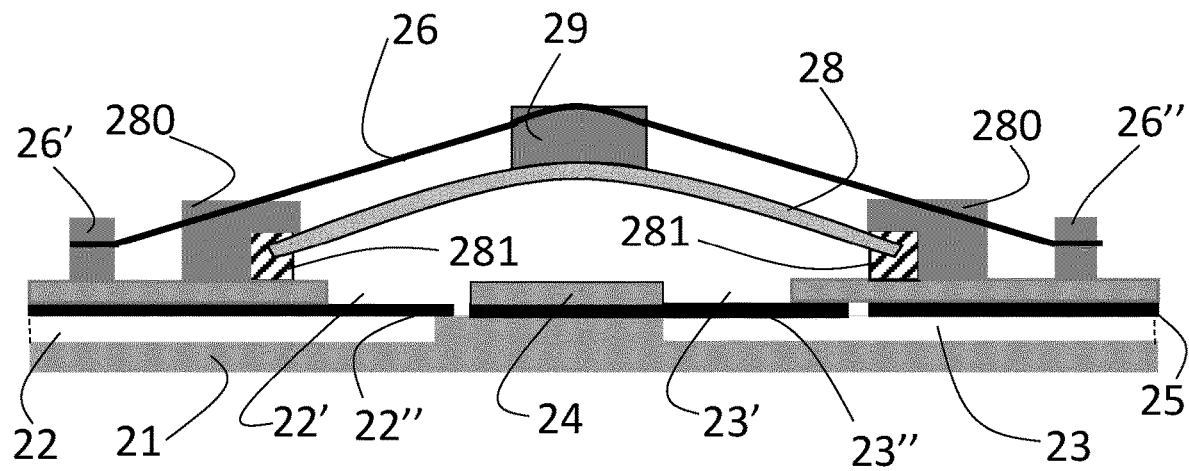
Figure 2C:
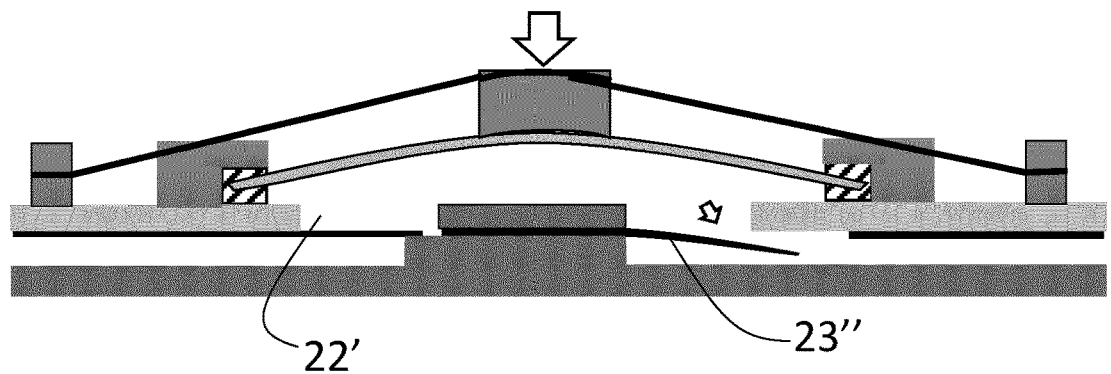
Figure 2D:
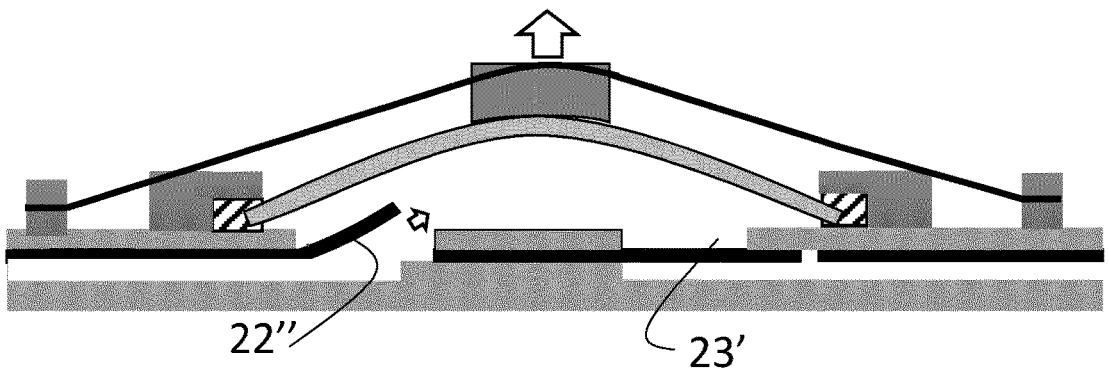

While FIG. 2B shows the cross-sectional schematic representation of subassembly 20 from a structural standpoint, FIGS. 2C and 2D show it during the fluid dispensing (FIG. 2C) and fluid loading (FIG. 2D) phases.

In particular, during the dispensing phase the activation of the shape memory alloy wire 26 results in a downward push on the deformable elastic element 28, preferably through a suitable coupler 29 located at the dome apex, thus reducing volume Vo toward V1 thanks to the deformation of element 28 allowed by the compressible gasket 281 housed in seat 280, i.e. the periphery of the deformable element 28 will dig deeper in the elastic gasket 281.

As in the first embodiment, the consequence of the pressure increase in the reservoir is that the outlet port 23' is opened because flap 23" is pushed down overcoming the resistance of membrane 25, thus enabling fluid communication between the reservoir and the outlet channel 23 (FIG. 2C). On the contrary, since flap 22" abuts from above on wall 24, the pressure increase will keep port 22' tightly closed thus preventing backflow of the fluid into the inlet channel 22.

Once the SMA wire 26 is deactivated, element 28 reverts to its original shape due to its elasticity and the push of gasket 281 along its periphery, thus restoring the maximum volume Vo. This results in a pressure decrease in the reservoir that leads to the closing of the outlet port 23', also thanks to the elasticity of flap 23" that returns to its undeformed position, and the opening of the inlet port 22' due to the upward deformation of flap 22".

As for the first embodiment, also in this case the subassembly needs to go through a first loading cycle in order to be ready for its following series of dispensing operations.

Figure 4:
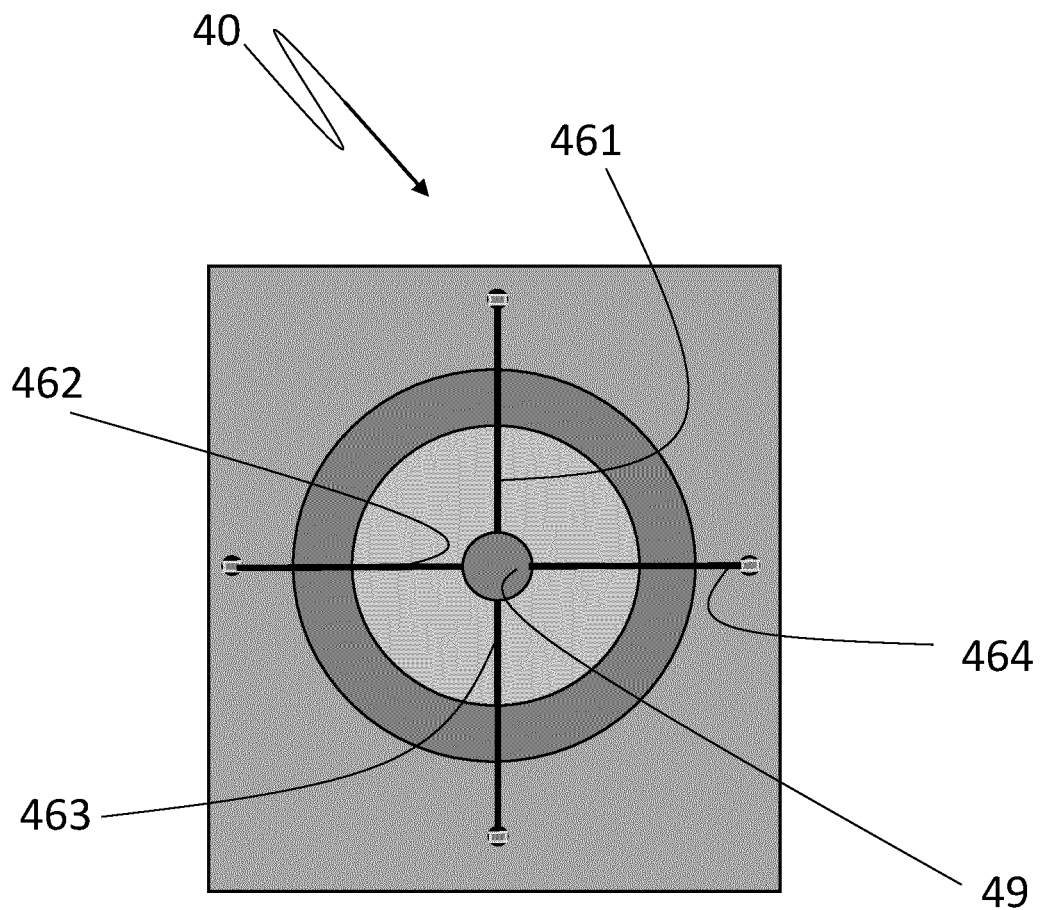
FIG. 4 is a schematic view from above of a variant of the second embodiment.

A variant of the second embodiment is represented in FIG. 4, showing a subassembly 40 that substantially has the same structure and operation of subassembly 20 shown in FIGS. 2A-2D but differs in the number of shape memory alloy wires. In fact, in subassembly 40 the actuation is provided by four SMA wires 461, 462, 463, 464 each with a first extremity connected to a common coupler 49 located at the apex of dome 28 and a second extremity connected to a respective fixing pillar.

Other possible variants not shown in the drawings could use only two aligned SMA wires, i.e. one of the pairs 461/463 or 462/464, or two orthogonally crossing SMA wires, i.e. SMA wire 26 and another one orthogonal thereto. Furthermore, the pivoted flaps 12", 13" of the first embodiment could be used in the second embodiment to replace the membrane flaps 22", 23" and vice versa. Also, the SMA wires 16, 16' of the first embodiment could be replaced and/or integrated with one or more SMA wires passing over lid 18 similarly to the SMA wire 26 of the second embodiment.

It is to be underlined that the term "flap" is not limited to any specific geometry or configuration but it encompasses any equivalent element capable of closing and opening inlet and outlet ports under the action of the pressure changes caused by the reservoir volume reduction from Vo toward V1 and the reservoir volume increase from V1 toward Vo, according to the mechanism explained above.

It is also to be underlined that the overall force of actuation is to be evaluated considering all the contributions acting on the SMA wire(s) that is/are the only active element(s) causing the compression of the fluid-tight reservoir. In the case of a single SMA wire it is the sum of all the return forces acting on the SMA wire, in the case of multiple SMA wires it is the sum of all the return forces acting separately or commonly on the different SMA wires.

Therefore, in the embodiment of FIG. 4 the force is to be considered the sum of all the return forces acting on wires 461, 462, 463, 464 from the common return elements, i.e. the elastically deformable element 28 and the peripheral gasket 281, while in the first embodiment the return forces are separately provided by the return springs 17, 17' and shell 17". It would also be possible to have additional elastic return means, e.g. the second embodiment might include a return spring arranged between wall 24 and dome 28.

The present invention sets the correct limits on the return force provided by the elastic means, such that the overall return force F of said elastic means, expressed in Newton, is given by $$\frac{Vo}{V1} * 0.1\, \text{N} \le F \le \frac{Vo}{V1} * 0.75\, \text{N}$$

wherein Vo/V1 is comprised between 2 and 5. For example, for a system operating with a 3.5 compression ratio (i.e. Vo/V1=3.5) the overall return force F acting on the SMA wire(s) should have an upper limit not above 2.625 N and a lower limit not below 0.35 N.

Operating with too low a return force, for example 0.1 N, will result in a limited pressure level which is insufficient to pump the fluid through the channels, as well as a too low pressure difference to reliably operate the inlet and outlet flaps, particularly in the case of membrane flaps. Operating at excessive forces, for examples 6 N, will require a high-force SMA wire with its limitation in actuation speed, as well as an increase in the requirements for its fixation and a voltage requirement which is above 5V, preventing the use of a standard USB source.

The preferred maximum volume Vo for the shape memory alloy actuated fluidic subassembly according to the present invention is comprised between 100 and 500 µl.

With regards to the inlet and outlet flaps, the preferred ones are the bendable flaps depicted in FIGS. 2B-2D, with a thickness comprised between 50 µm and 250 µm, and more preferably the flaps are obtained from cutouts in a membrane made of a material having a Young modulus comprised between 0.001 and 0.05 GPa.

Even though the present invention is not limited to any specific shape memory alloy, preferred is the use of Ni—Ti based alloys such as Nitinol that may exhibit alternately a superelastic behavior or shape memory alloy behavior according to its processing. The properties of Nitinol and methods allowing to achieve them are widely known to those skilled in the art, see e.g. the article "A Study of the Properties of a High Temperature Binary Nitinol Alloy Above and Below its Martensite to Austenite Transformation Temperature" by Dennis W. Norwich presented at the SMST 2010 conference.

Nitinol may be used as such or its characteristics in terms of transition temperature may be tailored by adding elements such as Hf, Nb, Pt, Cu. The proper choice of material alloy and its characteristics are commonly known by those skilled in the art, see for example the white paper "Fabrication Process and Characterization of NiTi Wires for Actuators" by Tuissi at al.

Also, the shape memory alloy wires may be used "per se" or with a coating/sheath to improve their thermal management, i.e. their cooling after being deactivated. The coating sheath may be uniform, such as described in U.S. Pat. No. 9,068,561 that teaches how to manage residual heat by resorting to an electrically insulating coating which is a heat conductor, while U.S. Pat. No. 6,835,083 describes a shape memory alloy wire having an enclosing sheath capable to improve cooling after every actuation cycle. Also a coating made with or containing phase changing materials, as described in U.S. Pat. No. 8,739,525, may be advantageously employed.

With regards to shape memory alloy wires diameters they are preferably comprised between 50 and 150 µm.

In a second aspect thereof, the invention consists in an equipment incorporating a dispensing device comprising a shape memory alloy actuated fluidic subassembly as previously described. Preferably, such device is a medicine (consumable) cartridge or an analytical equipment, more preferably for a lab-on-a-chip application.

The invention claimed is:

1. A shape memory alloy actuated fluidic subassembly comprising:
   a base with an inlet channel, an outlet channel and a channel separating wall;
   a compressible fluid-tight reservoir in communication with said inlet channel through an inlet port closed by an inlet flap, and with said outlet channel through an outlet port closed by an outlet flap;
   at least one shape memory alloy wire arranged so as to compress, upon activation, said fluid-tight reservoir from a maximum volume Vo to a minimum volume V1 by acting on a fluid-tight reservoir lid; and
   elastic return means to restore the compressible fluid-tight reservoir volume from V1 to Vo upon deactivation of said at least one shape memory alloy wire;
   wherein the overall return force F of said elastic return means, expressed in Newton, is given by the formula:

$$\frac{Vo}{V1} * 0.1\,\text{N} \le F \le \frac{Vo}{V1} * 0.75\,\text{N}$$

wherein Vo/V1 is 2-5.

2. A shape memory alloy actuated fluidic subassembly according to claim 1, wherein Vo is 100 µl-500 µl.

3. A shape memory alloy actuated fluidic subassembly according to claim 1, wherein the inlet and outlet flaps have a thickness of 50 µm-250 µm.

4. A shape memory alloy actuated fluidic subassembly according to claim 1, wherein the inlet flap is longer than the width of the inlet port and the outlet flap is longer than the width of the outlet port.

5. A shape memory alloy actuated fluidic subassembly according to claim 4, wherein the inlet flap is fixed above the inlet port and abuts on the bottom of the reservoir, and the outlet flap is fixed below the outlet port and abuts on the ceiling of the outlet channel.

6. A shape memory alloy actuated fluidic subassembly according to claim 5, wherein said flaps are rigid and fixed on a pivot point so as to rotate with respect to the base.

7. A shape memory alloy actuated fluidic subassembly according to claim 5, wherein the flaps are flexible and rigidly fixed to the base, the flap material preferably having a Young modulus of 0.001-0.05 GPa.

8. A shape memory alloy actuated fluidic subassembly according to claim 4, wherein the inlet flap is fixed below the inlet port and abuts on a portion of the channel separating wall extending toward the inlet channel, and the outlet flap is fixed below the outlet port and abuts on the ceiling of the outlet channel.

9. A shape memory alloy actuated fluidic subassembly according to claim 8, wherein the inlet flap and the outlet flap are obtained from a continuous elastic membrane with two cut-outs shaped as inverted Cs, said membrane being located on the ceiling of the channels and passing through the channel separating wall, the membrane material preferably having a Young modulus of 0.001-0.05 GPa.

10. A shape memory alloy actuated fluidic subassembly according to claim 1, wherein the lid is a rigid lid in contact with one or more elastic return elements acting in opposition with respect to the one or more shape memory alloy wires.

11. A shape memory alloy actuated fluidic module subassembly according to claim 10, wherein the elastic return elements comprise one or more springs and/or a rubber shell defining in its uncompressed state the maximum volume Vo.

12. A shape memory alloy actuated fluidic module subassembly according to any of claim 1, wherein the lid is a dome-shaped elastically deformable element whose periphery is blocked by a gasket held in an annular seat fixed to the base, and the at least one shape memory alloy wire passes over the apex of the lid and acts thereon preferably through a coupler located at its apex.

13. A shape memory alloy actuated fluidic subassembly according to claim 12, wherein the actuation is provided by four SMA wires each with a first extremity connected to a common coupler located at the apex of the dome-shaped lid and a second extremity connected to a respective fixing pillar.

14. Equipment incorporating a dispensing device comprising a shape memory alloy actuated fluidic subassembly according to claim 1, said equipment being a fluid dispenser.

15. Analytical system incorporating an equipment according to claim 14, said analytical system being a lab-on-a-chip.

* * * * *